United States Patent
Allard et al.

[19]

[11] Patent Number: 6,120,507
[45] Date of Patent: Sep. 19, 2000

[54] INSTRUMENT AND METHOD FOR SEATING PROSTHESIS

[75] Inventors: Randall N. Allard, Plymouth; David B. Willard, Warsaw, both of Ind.; Evan L. Flatow, New York, N.Y.

[73] Assignee: Bristol-Myers Squibb Company, New York, N.Y.

[21] Appl. No.: 09/240,945

[22] Filed: Jan. 29, 1999

[51] Int. Cl.⁷ .................................................. A61B 17/16
[52] U.S. Cl. ................................ 606/80; 606/84; 606/85
[58] Field of Search ............................ 606/79, 80, 81, 606/84, 85

[56] References Cited

U.S. PATENT DOCUMENTS

| | | | |
|---|---|---|---|
| 4,790,852 | 12/1988 | Noiles | 623/18 |
| 4,946,461 | 8/1990 | Fischer | 606/84 |
| 5,169,401 | 12/1992 | Lester et al. | 606/79 |
| 5,180,384 | 1/1993 | Mikhail | 606/80 |
| 5,314,479 | 5/1994 | Rockwood, Jr. et al. | 623/19 |
| 5,358,526 | 10/1994 | Tornier | 623/19 |
| 5,462,548 | 10/1995 | Pappas et al. | 606/80 |
| 5,486,177 | 1/1996 | Mumme et al. | 606/79 |
| 5,489,310 | 2/1996 | Mikhail | 623/19 |
| 5,520,692 | 5/1996 | Ferante | 606/80 |
| 5,536,271 | 7/1996 | Daly et al. | 606/80 |
| 5,540,694 | 7/1996 | DeCarlo, Jr. et al. | 606/80 |
| 5,575,793 | 11/1996 | Carls et al. | 606/80 |
| 5,658,290 | 8/1997 | Lechot | 606/80 |
| 5,658,291 | 8/1997 | Techiera | 606/80 |
| 5,709,688 | 1/1998 | Salyer | 606/81 |
| 5,716,362 | 2/1998 | Treacy | 606/87 |
| 5,728,161 | 3/1998 | Camino et al. | 623/19 |
| 5,980,170 | 11/1999 | Salyer | 606/80 |

OTHER PUBLICATIONS

Fenlin Total Shoulder Surgical Technique Brochure (97–4065–02) 1988 Zimmer, Inc.

*Primary Examiner*—Michael Buiz
*Assistant Examiner*—Julian W. Woo
*Attorney, Agent, or Firm*—Cory R. Reeves

[57] ABSTRACT

Instruments and a method are provided for reducing the gap between an implant head and the underlying resected bone surface to produce a more anatomic joint reconstruction. This is accomplished by providing a reamer for counter boring the resected surface to receive the collar so that a portion of the collar is recessed into the resected surface. The present invention permits the flexibility and stability of a collared two-piece implant while maintaining the close fit of a unitary implant.

4 Claims, 6 Drawing Sheets

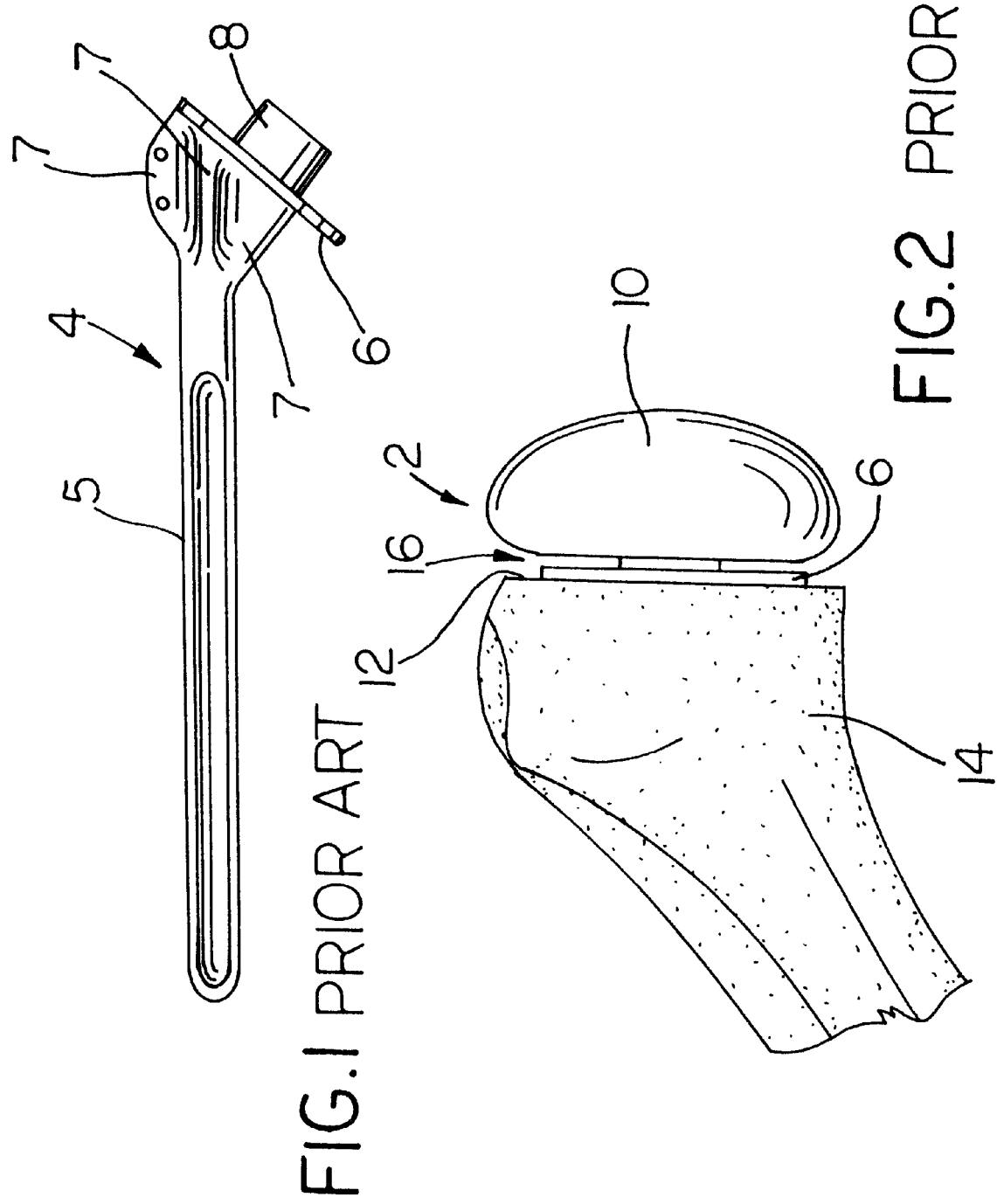

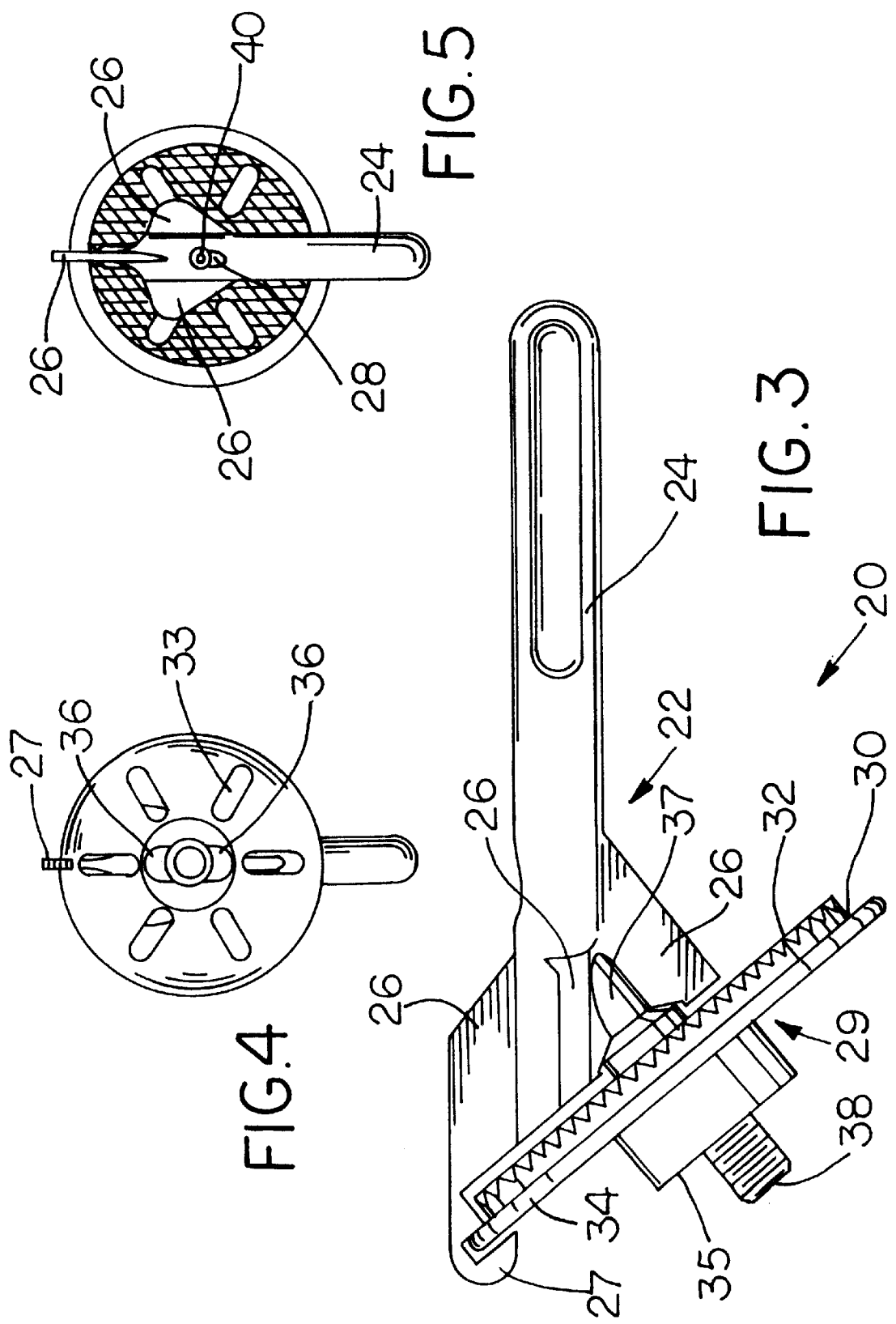

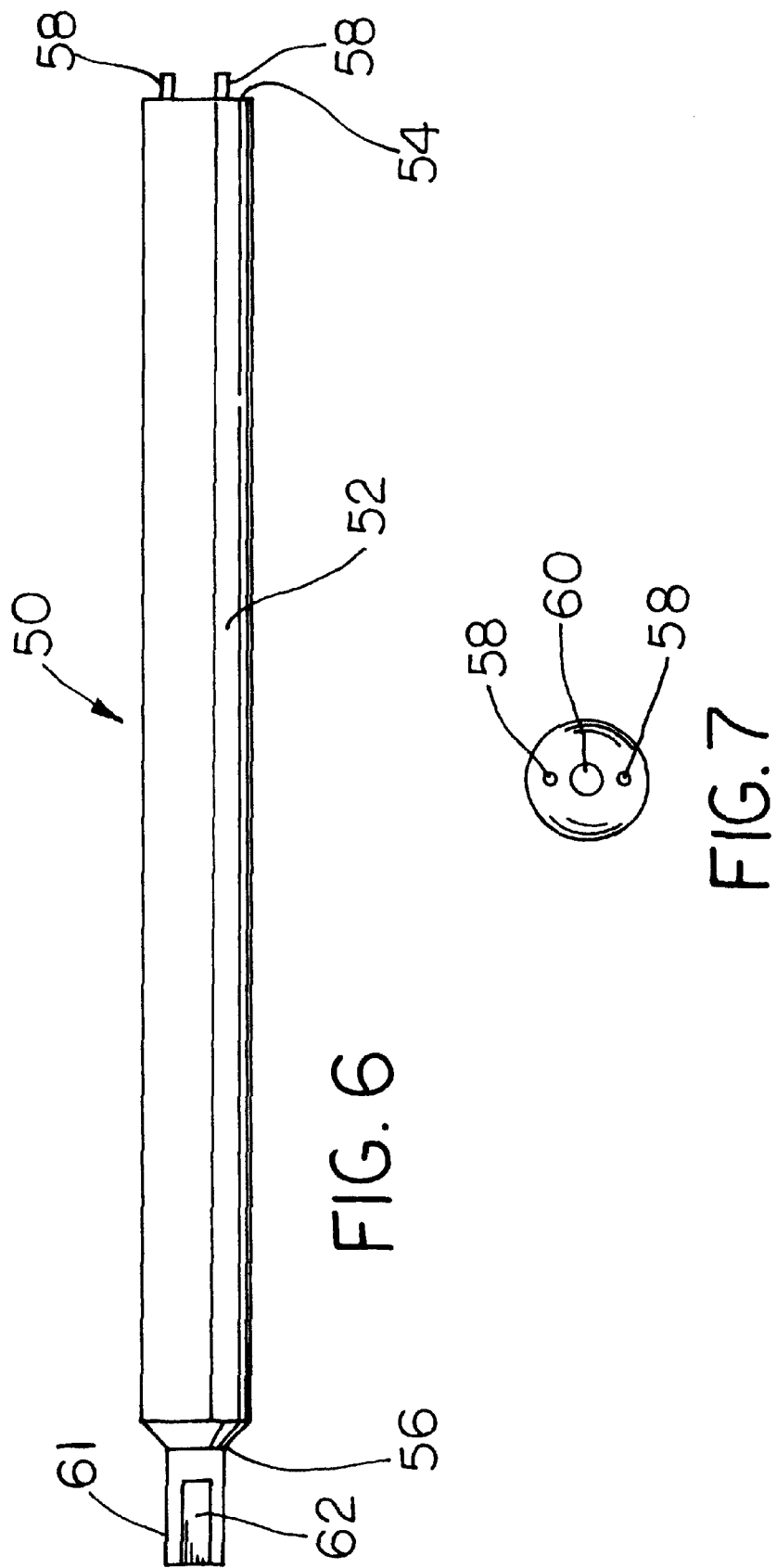

INSTRUMENT AND METHOD FOR SEATING PROSTHESIS

BACKGROUND OF THE INVENTION

The present invention relates to instruments and methods for implanting a prosthetic joint component. More particularly, the invention relates to instruments and methods for counter boring a long bone for receiving a stemmed and collared implant.

When trauma or disease result in damage to the articular surfaces of a joint, such as the shoulder, it is often necessary to replace the articulating portions of the bones with artificial joint components to restore function and relieve pain. For a long bone such as the humerus, such a replacement involves excising the humeral head to produce a flat seating surface, cannulating the shaft of the bone along the intramedullary canal with a reamer, and seating a humeral implant. Some implants are of a unitary construction with the head being integral with the stem. In that case the implant is seated with the stem in the intramedullary canal and the head seated on the flat surface where the head was resected.

Other implants are of a two-piece design in which the head and stem are connected together at the time of surgery. Two-piece implants provide additional choices with reduced inventory since various head configurations can be interchangeably matched with various stem configurations. Two-piece implants typically include a shoulder, or collar, on the stem that seats on the bone. The head then connects onto the stem above the collar thus isolating the head from the bone. Typically a gap exists between the underside of the head and the resected bone surface. FIGS. 1 and 2 depict a prior art two-piece implant 2 having a stem 4 including a shaft 5 and collar 6. Fins 7 project from the shaft 5 to provide rotational stability to the implant 2. Above the collar 6 is a male taper 8 for engaging a female taper of a head 10. The collar 6 rests against the resected surface 12 of the bone 14 and the shaft 5 lies in the reamed intramedullary canal of the bone. As can be seen in FIG. 2, the collar resting on the bone surface 12 results in a gap 16 between the head 10 and the surface 12.

SUMMARY OF THE INVENTION

The present invention includes instruments and a method for reducing the gap between an implant head and the underlying resected bone surface to produce a more anatomic joint reconstruction. This is accomplished by providing a reamer for counter boring the resected surface to receive the collar so that a portion of the collar is recessed into the resected surface. The present invention permits the flexibility and stability of a collared two-piece implant while maintaining the close fit of a unitary implant.

BRIEF DESCRIPTION OF THE DRAWINGS

FIG. 1 is a frontal view of a prior art collared two-piece humeral implant.

FIG. 2 is a frontal view of the implant of FIG. 1 mated with a head component and inserted in a humeral bone by a prior art technique.

FIG. 3 is a frontal view of the counter boring reamer according to the present invention.

FIG. 4 is a left side view of the reamer of FIG. 3.

FIG. 5 is a right side view of the reamer of FIG. 3.

FIG. 6 is a frontal view of a drive shaft according to the present invention.

FIG. 7 is a is a right side view of the drive shaft of FIG. 6.

DETAILED DESCRIPTION OF THE INVENTION

Figure 9:
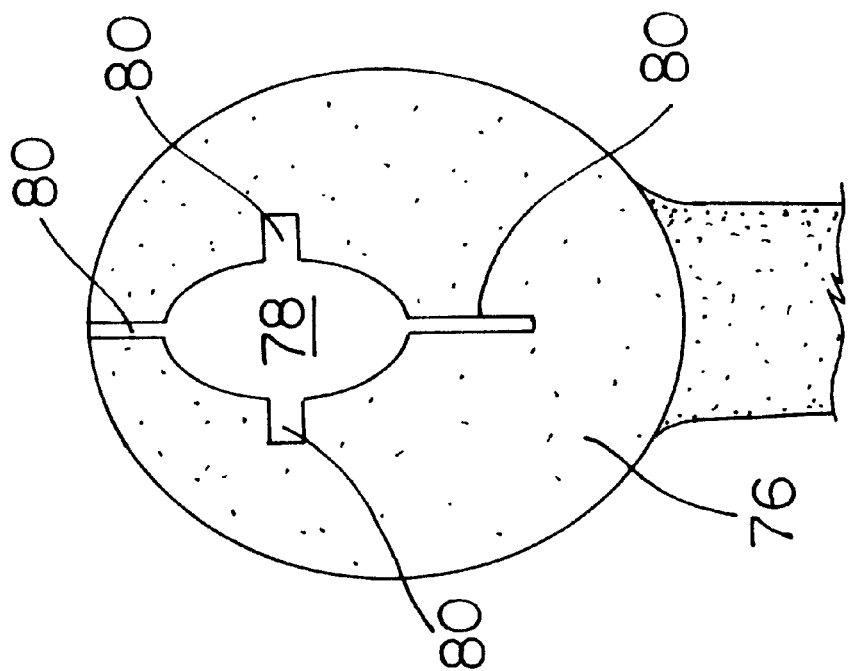
FIG. 9 is a right side view of the humeral bone of FIG. 8 showing the flat surface left after the head is resected and the cavity formed by reaming and broaching.
Figure 8:
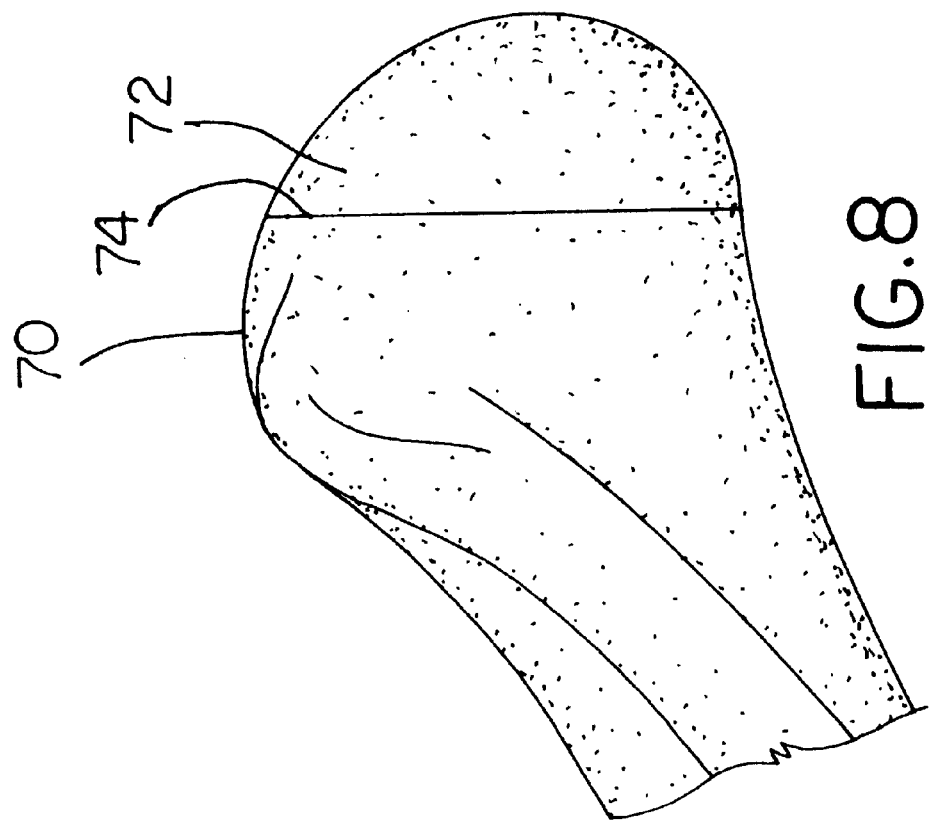
FIG. 8 is a frontal view of a humeral bone showing the cut line of the head resection.

FIGS. 3–7 depict an exemplary counter boring humeral reamer 20 according to the present invention. The reamer has a reamer body 22 including a stem 24 and fins 26. The reamer body 22 conforms to the shape and size of the proximal portion of an implant for which the reamer is used to prepare the implantation surface. In other words, the stem 24 diameter and fin 26 geometry are the same as those of a corresponding implant. A retaining tab 27 extends from the end of the body 24 adjacent the fins 26. A through hole 28 is formed in the proximal end of the body 22 along the axis of the center of the collar of a corresponding implant.

A reamer blade 29 includes a disc 30 having cutting teeth 32 arranged in a circular pattern and directed toward the reamer body 22. The diameter of the tooth pattern corresponds to the diameter of the implant collar. The disc includes clearance slots 33 arranged in a radial pattern. The back side of the disc 30 forms a circular shoulder 34 extending radially at the base of the tooth pattern such that it has a diameter greater than that of the tooth pattern. The depth of the teeth 32, as measured from the tips of the teeth to the shoulder 34, is equal to the thickness of the implant collar. An engagement boss 35 extends from the shoulder 34. The boss 35 includes engagement holes 36.

The disc 30 is mounted on a shaft 37 which is likewise mounted for rotation in the through hole 28. One end of the shaft 37 has a screw thread 38 and the opposite end has a hex head 40. The retaining tab 27 hooks over the shoulder 34 to retain the blade 29 on the body 24.

FIGS. 6 and 7 show a drive shaft 50 for driving the reamer 20. The drive shaft 50 includes an elongated body 52 with a reamer engaging end 54 and a driver engaging end 56. The reamer engaging end 54 includes protruding pins 58 for engaging the engagement holes 36 of the boss 35. The reamer engaging end 54 also includes a threaded hole 60 for receiving the screw thread 38 on the end of shaft 37. The driver engaging end 56 includes a nipple 61 having flat surfaces 62 formed on it for positive engagement such as by a Jacobs chuck on a drill.

The drive shaft 50 is assembled to the reamer 20 by aligning the pins 58 and hole 60 of the drive shaft 50 with the holes 36 and screw thread 38 of the reamer 20 and turning the shaft 37 via a screwdriver and hex head 40 to thread the parts together. The threaded junction 38,60 provides axial coupling while the pinned engagement 58,36 provides for non-slip driving of the blade 29.

FIGS. 8–13 depict the method according to the present invention. A humeral bone 70 is surgically exposed and is first prepared as is well known in the art. The head 72 is resected along line 74 to produce a flat surface 76. Next, a reamer is introduced through the surface 76 and directed along the intramedullary canal to ream the interior of the bone 70 so that a hole 78 is formed for receiving the implant stem. Finally, a broach is optionally inserted into the hole 78 to further form the proximal portion of the bone such as by cutting fin slots 80 if such features are included on the implant.

Figure 10:
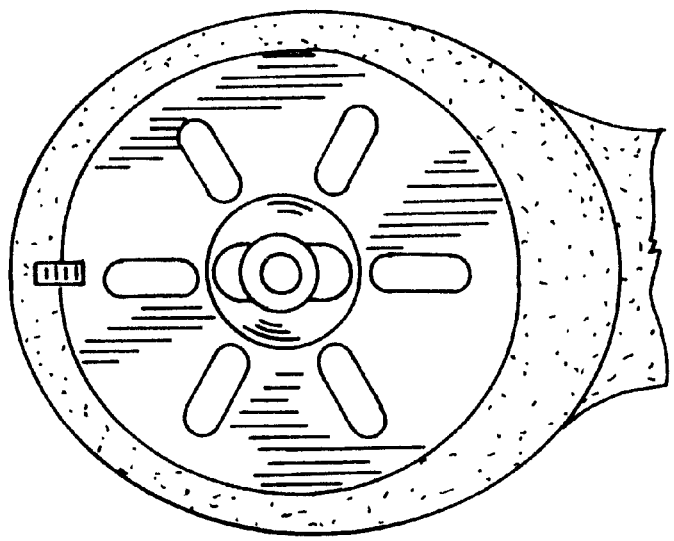
FIG. 10 is a right side view of the humeral bone of FIG. 8 showing the reamer of FIG. 3 placed on the bone after the preparation steps of FIG. 9.
Figure 11:
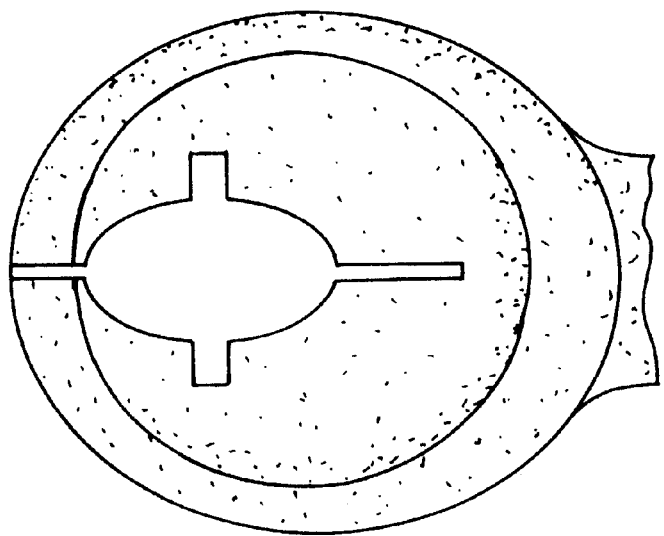
FIG. 11 is a right side view of the humeral bone of FIG. 8 showing the counter bore formed by the reamer.

The bone is further prepared in accordance with the present invention as shown in FIGS. 10–11. The reamer 20 is inserted into the hole 78 previously prepared. Since the reamer body 22 conforms to the shape and size of the proximal portion of the implant, the reamer seats in precisely the same position, both within the plane and rotationally, on the flat surface 76 as will the implant. Also, since the reamer body is the same size and shape as the proximal implant, the reamer will fit closely with the prepared canal of the bone and provide a stable reaming platform. FIG. 10 shows the reamer 20 in place on the bone. The drive shaft is not shown in this view for clarity. With the drive shaft 50 in place, the reamer is turned to cut a counter bore in the bone surface 76. As the teeth 32 remove bone, the bone chips flow through clearance slots 33 and the reamer 20 subsides into the bone. The progress of the reamer 20 into the bone is stopped when the shoulder 34 contacts the bone surface 76. The depth of the teeth is equal to the thickness of the implant collar so that the top of the collar will sit flush with the bone surface 76.

Figure 13:
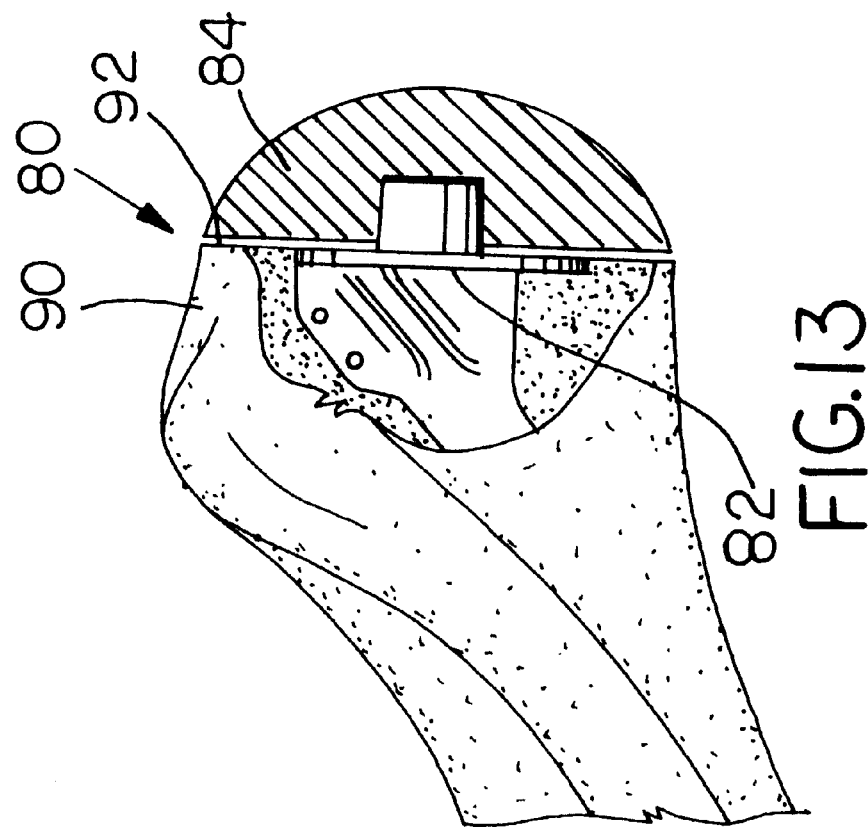
FIG. 13 is a partial sectional frontal view of the humeral bone and implant of FIG. 12.
Figure 12:
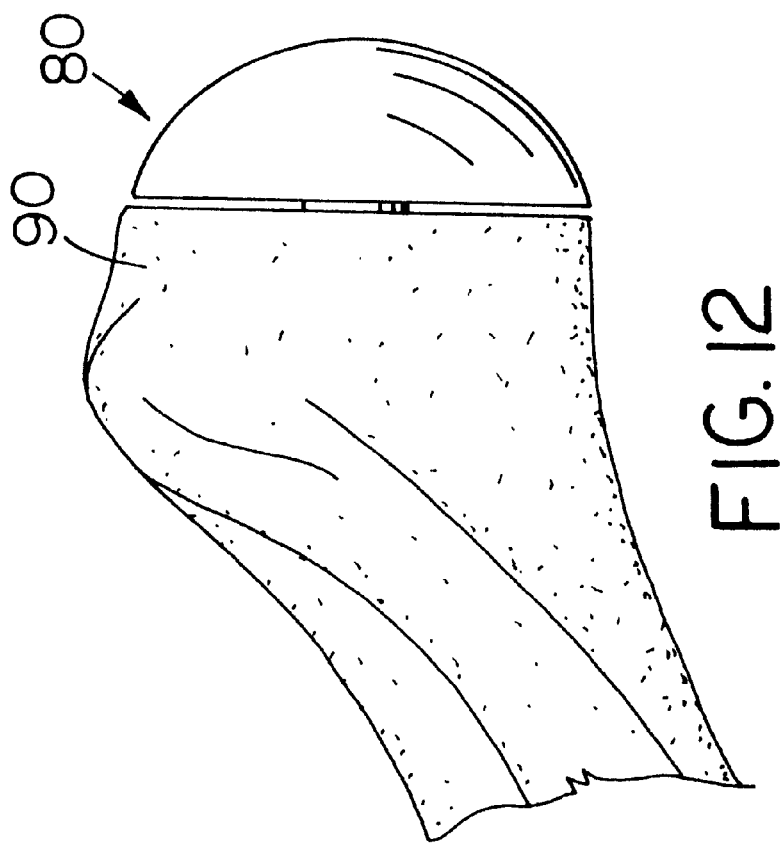
FIG. 12 is a frontal view of the humeral bone of FIG. 8 showing a collared two-piece humeral implant mated with a head component and seated in the bone according to the present invention.

FIGS. 12 and 13 show an implant 80 seated in a bone 90 according to the present invention. The implant collar 82 is seated in a counter bore to minimize the gap between the head 84 and the resected bone surface 92.

It will be understood by those skilled in the art that the foregoing has described a preferred embodiment of the present invention and that variations in design method steps may be made to the preferred embodiment without departing from the spirit and scope of the invention defined by the appended claims. For example, while the preferred embodiment made reference to a humeral implant, the invention is equally applicable to similarly stemmed and collared implants for other bones and joints. Likewise, while the preferred embodiment is for the cutter to be the same size and shape as the collar, it is also useful to ream a counter sink that is of a different size and shape. One such case may be where there is a rectangular or oval shaped collar. Such collars will have a major dimension rather than a diameter. As long as the reamer produces a counter bore with a diameter equal to or greater than the major dimension, the collar will fit within the counterbore. Also, while in the preferred embodiment the axis of the reamer blade coincided with the axis of the collar, this need not be the case so long as the counter bore is sufficiently large to receive the collar. Finally, while the preferred embodiment described a shoulder formed on the blade for stopping the blade at a depth for seating the collar flush, other stop means are possible within the scope of the invention. The depth can be controlled manually by the operator or by means associated with the drive shaft. Likewise, the collar can be set at any desired height, above or below flush, by the method of the invention.

What is claimed is:

1. A counter bore reamer for preparing a resected surface of a bone to receive a stemmed implant, the bone having an intramedullary canal, the implant having a collar with a major dimension and a thickness, the reamer comprising:

a body configured for mounting in said intramedullary canal adjacent said resected surface of said bone; and a blade mounted for rotation on the body, the body supporting the blade in cutting relation to said resected surface of said bone, the blade having on one side a tooth pattern directed toward the body with outer cutting tips and a diameter greater than or equal to said major dimension of said implant collar wherein rotation of the blade relative to the body is operative to cut a counter bore into said resected bone surface for receiving said implant collar, the reamer further comprising means for limiting the depth that the reamer blade penetrates into said bone, wherein the means for limiting the depth comprises a shoulder extending radially from the base of the tooth pattern.

2. The reamer of claim 1 wherein the blade has a tooth depth as measured from the outer cutting tips to the shoulder corresponding to said thickness of said implant collar.

3. A counter bore reamer for preparing a resected surface of a proximal humeral bone to receive a stemmed humeral implant having a stem and a collar, the bone having an intramedullary canal and having been reamed and broached to closely receive the implant, the implant having a collar with a major dimension and a thickness, the reamer comprising:

a body having a stem corresponding in shape to a portion of said stemmed humeral implant, the body being configured for a close fit within said reamed and broached intramedullary canal; and a blade mounted for rotation on the body, the body supporting the blade in cutting relation to said resected surface of said bone, the blade having on one side a tooth pattern directed toward the body with outer cutting tips and a diameter greater than or equal to said major dimension of said humeral implant collar, the blade having a shoulder extending radially from the base of the tooth pattern, the blade having a tooth depth as measured from the outer cutting tips to the shoulder along the axis corresponding to a said thickness of said humeral implant collar wherein rotation of said blade relative to said body is operative to cut a counter bore into said resected bone surface to a depth equal to the thickness of said implant collar for receiving said implant collar in flush seating relation.

4. A method for preparing a humeral bone for receiving a stemmed humeral implant having a collar with a diameter and a thickness, the method comprising the steps of:

excising the humeral head to produce a flat surface;

reaming the intramedullary canal of the humeral bone;

providing a counter boring reamer comprising a body configured for mounting in the intramedullary canal of the humeral bone adjacent the resected surface of the proximal humeral bone and a blade mounted for rotation about an axis on the body, the blade having on one side a tooth pattern directed toward the body with outer cutting tips and a diameter corresponding to the diameter of the humeral implant collar, the blade having a shoulder extending radially from the base of the tooth pattern, the blade having a tooth depth as measured from the outer cutting tips to the shoulder along the axis corresponding to the thickness of a said humeral implant collar;

mounting the reamer with the body in the intramedullary canal and the blade directed against the flat surface;

reaming until the blade shoulder seats on the flat surface to form a reamed recess;

removing the reamer; and seating the humeral implant so that the collar lies in the reamed recess with the top of the collar flush with the flat surface.

\* \* \* \* \*